United States Patent
Bunch et al.

(10) Patent No.: US 10,549,130 B2
(45) Date of Patent: Feb. 4, 2020

(54) MAGNESIUM BATH SALT

(71) Applicant: Nutraceutical Corporation, Park City, UT (US)

(72) Inventors: David E. Bunch, Kaysville, UT (US); Frank W. Gay, II, Park City, UT (US); Autumn Blum, Wauchula, FL (US); Antoine Nkameni, Sebring, FL (US)

(73) Assignee: Nutraceutical Corporation, Park City, UT (US)

( * ) Notice: Subject to any disclaimer, the term of this patent is extended or adjusted under 35 U.S.C. 154(b) by 183 days.

(21) Appl. No.: 14/605,539

(22) Filed: Jan. 26, 2015

(65) Prior Publication Data

US 2016/0213710 A1    Jul. 28, 2016

(51) Int. Cl.
*A61Q 19/10*    (2006.01)

(52) U.S. Cl.
CPC .................................. *A61Q 19/10* (2013.01)

(58) Field of Classification Search
None
See application file for complete search history.

(56) References Cited

U.S. PATENT DOCUMENTS

| | | |
|---|---|---|
| 1,465,530 A | 8/1923 | Smith |
| 2,084,465 A | 6/1937 | Stoughton |
| 4,342,743 A | 8/1982 | Panton-Moore |
| 5,602,178 A * | 2/1997 | Caroselli .................. A61K 8/37 514/529 |
| 5,958,462 A | 9/1999 | McLean |
| 2014/0079896 A1 | 3/2014 | Slaboden |

FOREIGN PATENT DOCUMENTS

| | | | |
|---|---|---|---|
| CN | 102451092 | * | 5/2012 |
| DE | 102012102334 | | 9/2013 |
| EP | 0 439 640 | | 8/1991 |
| EP | 0 716 851 | | 6/1996 |
| EP | 1 874 689 | | 1/2008 |

OTHER PUBLICATIONS

Pure Magnesium Flakes 4 oz., Life-Flo Health Care, date unknown (See "Date Information" section below for more information) (4 pp.).
Magnesium Chloride Flakes, Swanson Health Products, date unknown (See "Date Information" section below for more information) (2 pp.).

* cited by examiner

*Primary Examiner* — David J Blanchard
*Assistant Examiner* — Sarah J Chickos
(74) *Attorney, Agent, or Firm* — Holland & Hart, LLP

(57) ABSTRACT

A bath salt contains granular magnesium chloride material that is uniformly coated with a fragrance enhancing material and/or a colorant. The bath salt can include magnesium sulfate material and mineral salt material. The bath salt can be made by mixing the magnesium chloride material and starch material to form an intermediate mixture. The colorant and the intermediate mixture are mixed together to form a uniformly colored bath salt.

20 Claims, 1 Drawing Sheet

MAGNESIUM BATH SALT

BACKGROUND

Bath and bathing therapies have been known for centuries. Thousands of years ago, wealthy families used scented and anointed waters to alleviate a virtual array of ailments ranging from minor muscular discomfort to life-threatening disease.

This trend continues today with the widespread use of commercially available bath salts. People use them to look more beautiful and smell great. People also use them to improve their mood and overall well-being.

Bath salts benefit the skin in many ways. Bath salts contain many beneficial minerals and nutrients that keep the skin smooth, soft, and supple. Some of the minerals found in bath salts include magnesium, potassium, calcium, bromide, and sodium. These minerals are easily absorbed into pores and cleanse and purify the skin on a molecular level, improving the skin's radiance, tone, and texture.

The minerals in bath salts can provide a variety of benefits. Magnesium helps fight stress and combat fatigue. Calcium keeps water retention in check, promotes healthy bones, and can help stave off osteoporosis. Potassium balances moisture levels in the skin. Bromide soothes tired, sore muscles. Sodium plays a significant role in managing the balance of lymphatic fluid in our bodies. Bath salts benefit not only the skin, but the entire body.

Bath salts can also help detoxify the skin. Warm water opens the pores, allowing the minerals in the bath salts to deeply cleanse the skin. Bathing in a solution of warm water and bath salts draws out impurities, pollution, oil and dirt from the skin. Bath salts can even bring the added benefit of looking younger. Regular use of bath salts and bathing decreases the appearance of fine lines by plumping the skin and balancing moisture.

The benefits of bath salts are not just skin deep. Bath salts harvested from the dead sea have been shown to effectively treat and manage symptoms of osteoarthritis and tendinitis. In recent studies, people with these conditions were given a dead sea salt bath solution at levels of 0.5, 7.5 and 2 percent dead sea salt concentration. The condition of those who received a solution with more dead sea salt improved after just a few weeks of treatment. In various studies, regular bathing in bath salts for as little as a few weeks has reduced or eliminated symptoms such as itchiness, insomnia and psoriasis in patients.

The benefits of bath salts extend beyond the time in the tub. After bathing, people feel calm, relaxed, and happy. Bath salts infused with essential oils such as lavender or chamomile can soothe people and prepare them for a good night's sleep. If people take a bath first thing in the morning, bath salts infused with citrus or green tea essential oils perk them up so they can begin the day with focus and energy.

Magnesium chloride is one type of traditional bath salt. It provides many of the benefits already mentioned but suffers from a number of drawbacks. For example, it cannot be uniformly dyed other colors or effectively scented. This has limited the use of magnesium chloride as a bath salt.

SUMMARY

A bath salt and method for making it are disclosed. The bath salt includes granular magnesium chloride material that is uniformly coated with a fragrance enhancing material and/or a colorant. The bath salt is a stable formulation that has a uniform, colored appearance and a uniform scent.

The bath salt provides the benefits of magnesium combined with other salts in a free flowing, colored, and fragranced formulation. This was not possible with conventional formulations because the natural fragrances and colors do not readily adhere to the magnesium chloride material causing a sticky formulation or one with clumps.

The bath salt can also include additional salt materials such as granular magnesium chloride material and/or granular mineral salt material. The mineral salt material can include any suitable material. In one embodiment, the mineral salt material includes a natural salt such as dead sea salt. Other salt materials can be included as well.

The bath salt can include any suitable fragrance enhancing material and/or colorant. In one embodiment, the fragrance enhancing material includes an essential oil material. The bath salt can have a bright yellow, orange, purple, or green color.

The bath salt can be made using any suitable method. In one embodiment, the bath salt is made by forming a mixture of the magnesium chloride material and an additional salts such as magnesium sulfate material and/or mineral salt material. The salt mixture is combined with a fragrance enhancing material and a starch material to form an intermediate mixture. The intermediate mixture is mixed with a colorant to form the bath salt. The starch material enables the colorant and/or fragrance enhancing material to uniformly adhere to the surface of the magnesium chloride material as well as the other salt materials.

The Summary is provided to introduce a selection of concepts in a simplified form that are further described below in the Detailed Description. The Summary and the Background are not intended to identify key concepts or essential aspects of the disclosed subject matter, nor should they be used to constrict or limit the scope of the claims. For example, the scope of the claims should not be limited based on whether the recited subject matter includes any or all aspects noted in the Summary and/or addresses any of the issues noted in the Background.

DRAWINGS

The preferred and other embodiments are disclosed in association with the accompanying drawings in which:

FIG. 1 is a photograph of five jars of different colored magnesium scented bath salts arranged roughly in a circle. The jars contain the following colors of salts beginning with the top jar (12 o'clock position) and moving clockwise: green, purple, orange, yellow, and light brown.

DETAILED DESCRIPTION

A bath salt includes magnesium chloride material and/or other salt material that is scented and/or dyed one or more colors. In addition to the magnesium chloride material, the bath salt can include salt materials such as magnesium sulfate material and mineral salt material.

The bath salt is a stable, free flowing granular material that is not sticky or clumpy. The bath salt is stable meaning that it will retain its scent and/or color for a commercially acceptable period of time despite being exposed to direct sunlight and/or dramatic temperature swings during storage and the like.

In one embodiment, the bath salt is free flowing and does not aggregate together over long periods of time in storage. In another embodiment, the bath salt is free flowing but may aggregate together slightly during long term storage. In this situation, the aggregated bath salts can be easily broken up by gently shaking the container to restore the bath salt to a free flowing state.

The bath salt readily dissolves in water. The rate at which the bath salt dissolves in water is dependent on a number of factors. One factor is particle size. Larger particles tend to dissolve more slowly than smaller particles. Another factor is the composition and physical properties of the bath salt. Some salt material dissolves faster than others.

In one embodiment, the bath salt includes salt material having an average particle size of 1 mm to 8 mm, 2 mm to 6 mm, or 2.5 mm to 4 mm. In another embodiment, the bath salt includes salt material having an average particle size of at least 1 mm, at least 1.5 mm, at least 2 mm, or at least 2.5 mm. In another embodiment, the bath salt include salt material having an average particle size of no more than 8 mm, no more than 6 mm, or no more than 4 mm. It should be noted that the particle sizes are given based on the average of a volume distribution determined using a mesh sieve.

In one embodiment, the bath salt completely dissolves in 100° F. water in 2 minutes to 12 minutes, 3 minutes to 10 minutes, or 4 minutes to 8 minutes. In another embodiment, the bath salt completely dissolves in 100° F. water in no more than 2 minutes, no more than 3 minutes, no more than 4 minutes, no more than 5 minutes, no more than 7 minutes, no more than 10 minutes, or no more than 12 minutes.

The bath salt can include natural or non-natural materials. In one embodiment, the bath salt includes all natural materials. For example, the salt materials can be obtained directly from natural deposits of the material. The fragrance enhancing material and/or the colorants can also be obtained from natural sources. For example, the fragrance enhancing material and/or colorants can include materials that have not been genetically modified or obtained from genetically modified organisms.

The bath salt can include a variety of materials and have a variety of compositions. In one embodiment, the bath salt includes salt materials, fragrance enhancing materials, and/or colorants. For example, as mentioned above, the bath salt can include salt materials such as magnesium chloride material, magnesium sulfate material, mineral salt material, sodium bicarbonate material, and sodium hexametaphosphate material.

The magnesium chloride material can be any suitable material that contains magnesium chloride and/or its various hydrates. One example of suitable magnesium chloride material is magnesium bath flakes. The magnesium flakes can be broken or ground to a suitable size prior to use in the bath salt. Another example is the natural mineral bischofite. Magnesium chloride material can also be obtained from ancient seabeds such as the Zechstein seabed in northwest Europe.

The magnesium chloride material can have any of the particle sizes described above for the bath salts as a whole. The magnesium chloride material can also dissolve in water under the conditions given above for the bath salts as a whole.

The magnesium chloride material can include any suitable amount of magnesium chloride along with a variety of other materials, typically salts and especially mineral salts. It should be appreciated that natural mineral deposits of magnesium chloride can, and often do, include other minerals. Thus, the magnesium chloride material can include these other materials.

In general, it is preferable for the magnesium chloride material to contain at least a predominant amount of magnesium chloride. In other words, the magnesium chloride is the predominant component in the magnesium chloride material. In one embodiment, the magnesium chloride material can be entirely or almost entirely magnesium chloride.

In one embodiment, the magnesium chloride material includes 10 wt % to 100 wt % magnesium chloride or 50 wt % to 100 wt % magnesium chloride. In another embodiment, the magnesium chloride includes at least 10 wt % magnesium chloride, at least 20 wt % magnesium chloride, at least 30 wt % magnesium chloride, at least 40 wt % magnesium chloride, at least 50 wt % magnesium chloride, at least 60 wt % magnesium chloride, at least 70 wt % magnesium chloride, at least 80 wt % magnesium chloride, at least 90 wt % magnesium chloride, or at least 95 wt % magnesium chloride. In another embodiment, the magnesium chloride material includes at least 97 wt % magnesium chloride, at least 98 wt % magnesium chloride, or at least 99 wt % magnesium chloride.

The bath salt can include any suitable amount of the magnesium chloride material. In one embodiment, the bath salt includes 20 wt % to 99 wt % magnesium chloride material, 25 wt % to 95 wt % magnesium chloride material, or 40 wt % to 90 wt % magnesium chloride material. In another embodiment, the bath salt includes at least 20 wt % magnesium chloride material, at least 25 wt % magnesium chloride material, at least 30 wt % magnesium chloride material, at least 35 wt % magnesium chloride material, at least 40 wt % magnesium chloride material, at least 45 wt % magnesium chloride material, or at least 50 wt % magnesium chloride material. In another embodiment, the bath salt includes no more than 99 wt % magnesium chloride material, no more than 95 wt % magnesium chloride material, or no more than 90 wt % magnesium chloride material.

The magnesium sulfate material can be any suitable material that contains magnesium sulfate and/or its various hydrates. One example of suitable magnesium sulfate material is the mineral epsomite, which is commonly called Epsom salt. Another example is the natural mineral kieserite. The magnesium sulfate material can be broken or ground to a suitable size prior to use in the bath salt.

The magnesium sulfate material can have any of the particle sizes described above for the bath salts as a whole. The magnesium sulfate material can also dissolve in water under the conditions given above for the bath salts as a whole.

The magnesium sulfate material can include any suitable amount of magnesium sulfate along with a variety of other materials, typically salts and especially mineral salts. It should be appreciated that natural mineral deposits of magnesium sulfate can, and often do, include other minerals. Thus, the magnesium sulfate material can include these other materials.

In general, it is preferable for the magnesium sulfate material to contain at least a predominant amount of magnesium sulfate. In other words, the magnesium sulfate is the predominant component in the magnesium sulfate material. In one embodiment, the magnesium sulfate material can be entirely or almost entirely magnesium sulfate.

In one embodiment, the magnesium sulfate material includes 10 wt % to 100 wt % magnesium sulfate or 50 wt % to 100 wt % magnesium sulfate. In another embodiment, the magnesium sulfate includes at least 10 wt % magnesium sulfate, at least 20 wt % magnesium sulfate, at least 30 wt % magnesium sulfate, at least 40 wt % magnesium sulfate, at least 50 wt % magnesium sulfate, at least 60 wt % magnesium sulfate, at least 70 wt % magnesium sulfate, at least 80 wt % magnesium sulfate, at least 90 wt % magnesium sulfate, or at least 95 wt % magnesium sulfate. In another embodiment, the magnesium sulfate material includes at least 97 wt % magnesium sulfate, at least 98 wt % magnesium sulfate, or at least 99 wt % magnesium sulfate.

The bath salt can include any suitable amount of the magnesium sulfate material. In one embodiment, the bath salt includes 2 wt % to 50 wt % magnesium sulfate material, 5 wt % to 40 wt % magnesium sulfate material, or 10 wt % to 30 wt % magnesium sulfate material. In another embodiment, the bath salt includes at least 2 wt % magnesium sulfate material, at least 5 wt % magnesium sulfate material, at least 10 wt % magnesium sulfate material, or at least 15 wt % magnesium sulfate material. In another embodiment, the bath salt includes no more than 50 wt % magnesium sulfate material, no more than 40 wt % magnesium sulfate material, or no more than 30 wt % magnesium sulfate material.

The mineral salt material can be any suitable material that contains mineral salt. One example of suitable mineral salt material is dead seat salt. The dead sea salt can be broken or ground to a suitable size prior to use in the bath salt. Mineral salt material can also be obtained from sources such as the Great Salt Lake in Utah.

The mineral salt material can have any of the particle sizes described above for the bath salts as a whole. The mineral salt material can also dissolve in water under the conditions given above for the bath salts as a whole.

The mineral salt material can include a variety of salt material including sodium, potassium, and calcium chlorides as well as bromides. It should be appreciated that natural mineral deposits of mineral salt can, and often do, include a wide variety of materials. Thus, the mineral salt material can include these other materials.

The bath salt can include any suitable amount of the mineral salt material. In one embodiment, the bath salt includes 1 wt % to 30 wt % mineral salt material, 3 wt % to 25 wt % mineral salt material, or 5 wt % to 20 wt % mineral salt material. In another embodiment, the bath salt includes at least 1 wt % mineral salt material, at least 3 wt % mineral salt material, or at least 5 wt % mineral salt material. In another embodiment, the bath salt includes no more than 30 wt % mineral salt material, no more than 25 wt % mineral salt material, or no more than 20 wt % mineral salt material.

It should be appreciated that each one of the magnesium chloride material, magnesium sulfate material, and the mineral salt material can be included as physically separate granular components even though, for example, the mineral salt material may contain some amount of magnesium chloride or magnesium sulfate.

The bath salt can include any suitable fragrance enhancing material. In one embodiment, the fragrance enhancing material includes an essential oil material that provides a pleasing scent. Examples of suitable essential oils include agar oil, balsam oil, eucalyptus oil, cedarwood oil, jasmine oil, lavender oil, lemon oil, orange oil, rose oil, sandalwood oil, and the like.

The bath salt can also use any suitable colorant to impart a distinctive and aesthetically pleasing color. In one embodiment, the colorant is a natural colorant.

The bath salt also includes a starch material that helps the fragrance enhancing material and the colorant to adhere and uniformly coat the salt material. The starch material can be any suitable starch material. In one embodiment, the starch material includes corn starch. In another embodiment, the starch material includes tapioca starch.

The bath salt can be made using any suitable method. It should be appreciated, however, that the salt material and particularly the magnesium chloride material can be relatively delicate so it is preferable to minimize the amount of mixing (e.g., tumbling) required to make the bath salt to prevent the salt materials from being broken into undesirably small particles.

The first step is to size the particles of the salt materials. This can include grinding or otherwise breaking the particles until they are the desired size. This can also include sieving the particles to remove particles that are too large or too small. This step can be skipped if the salt materials already have the desired particle size.

The second step is mix the salt materials together. In those embodiments that include magnesium chloride material, magnesium sulfate material, and mineral salt material, this step includes mixing those materials together. In one embodiment, this is done by gently tumbling the materials.

The third step is to add the fragrance enhancing material to the salt materials and mix them together. This can be done by gently tumbling the materials to avoid damaging them. The fourth step is to add the starch material to the mixture and gently tumble it to thoroughly mix it.

The colorant is added next and the mixture is gently tumbled until it has a uniform color. If the colorant is a solid, then it is mixed with water before being mixed with the salt materials.

It should be appreciated that the various steps disclosed in this method can be combined and/or eliminated as desired. For example, the fragrance enhancing material can be left out of the bath salt by omitting the step where it is added. Also, the starch material can be added with the colorant although doing so is not preferred because it requires additional tumbling that can damage the physical structure of the salt materials, particularly the magnesium chloride material.

EXAMPLES

The following examples are provided to further illustrate the disclosed subject matter. They should not be used to constrict or limit the scope of the claims in any way.

Example 1

A yellow magnesium scented bath salt was prepared having the formula in Table 1. The magnesium chloride, magnesium sulfate, and dead sea salt were processed to remove particles larger than approximately 3.7 mm and smaller than approximately 2.5 mm. This was done by passing these materials through a 6 mesh sieve and an 8 mesh sieve, respectively. The magnesium chloride flakes were ground before being separated.

TABLE 1

| Yellow Magnesium Scented Bath Salt Formulation | | |
|---|---|---|
| Material | Wt % | Kg in Batch |
| Magnesium Chloride (Magnesium Flakes) | 66.75 | 33.375 |
| Magnesium Sulfate (Epsom Salt) | 20 | 10 |
| Mineral Salt Source (Dead Sea Salt) | 10 | 5 |
| Natural Fragrance (Citrus Fruit) | 0.75 | 0.375 |
| Corn Starch (Farmal CS 3757) | 1.5 | 0.75 |
| Water (Deionized) | 0.5 | 0.25 |
| Natural Yellow Colorant (Turmeric Extract CI 75300) | 0.5 | 0.25 |

The magnesium chloride, magnesium sulfate, and the dead sea salt were weighed out in the amounts shown in Table 1 and combined. The resulting mixture was gently tumbled for about 5 minutes. The salts were gently tumbled to avoid destroying the structure of the salts.

The natural fragrance was slowly and gradually added to the salt mixture followed by gentle tumbling for 7-10 minutes. The corn starch was added to the salt mixture followed by gentle tumbling for 5 minutes. The water and natural yellow color were premixed and then slowly added to the salt mixture followed by gentle tumbling until the salt mixture had a uniform yellow color.

The resulting salt mixture was allowed to sit for 48 hours. After that time, the salt mixture was shaken for 5 minutes to separate the aggregates. The mixture was placed into appropriate containers.

Example 2

An orange magnesium scented bath salt was prepared having the formula in Table 2. The procedure was the same as that described in Example 1.

TABLE 2

Orange Magnesium Scented Bath Salt Formulation

| Material | Wt % | Kg in Batch |
| --- | --- | --- |
| Magnesium Chloride (Magnesium Flakes) | 66.75 | 33.375 |
| Magnesium Sulfate (Epsom Salt) | 20 | 10 |
| Mineral Salt Source (Dead Sea Salt) | 10 | 5 |
| Natural Fragrance (Orange Twist) | 0.75 | 0.375 |
| Corn Starch (Farmal CS 3757) | 1.5 | 0.75 |
| Water (Deionized) | 0.5 | 0.25 |
| Natural Orange Colorant (Annatto Seed Extract CI 75120) | 0.5 | 0.25 |

Example 3

A green magnesium scented bath salt was prepared having the formula in Table 3. The procedure was the same as that described in Example 1 except there is no water to premix with the colorant.

TABLE 3

Green Magnesium Scented Bath Salt Formulation

| Material | Wt % | Kg in Batch |
| --- | --- | --- |
| Magnesium Chloride (Magnesium Flakes) | 67.7 | 33.85 |
| Magnesium Sulfate (Epsom Salt) | 20 | 10 |
| Mineral Salt Source (Dead Sea Salt) | 10 | 5 |
| Natural Fragrance (*Eucalyptus Globulus* Leaf Essential Oil) | 0.5 | 0.25 |
| Corn Starch (Farmal CS 3757) | 1.5 | 0.75 |
| Natural Green Colorant (Sodium Copper Chlorophyllin CI 75810) | 0.3 | 0.15 |

Example 4

A lavender magnesium scented bath salt was prepared having the formula in Table 4. The procedure is the same as that described in Example 3.

TABLE 4

Lavender Magnesium Scented Bath Salt Formulation

| Material | Wt % | Kg in Batch |
| --- | --- | --- |
| Magnesium Chloride (Magnesium Flakes) | 66.95 | 33.475 |
| Magnesium Sulfate (Epsom Salt) | 20 | 10 |
| Mineral Salt Source (Dead Sea Salt) | 10 | 5 |
| Natural Fragrance (Lavender Oil) | 0.75 | 0.375 |
| Corn Starch (Farmal CS 3757) | 2 | 1 |
| Natural Purple Colorant (Purple Color Carmine Liquid) | 0.3 | 0.15 |

Examples 1-4 all yielded a bath salt of uniform color and fragrance. The bath salts were aesthetically pleasing to view and smell.

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure the term shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope.

The subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be given their broadest interpretation in view of the prior art and the meaning of the claim terms.

As used herein, spatial or directional terms, such as "left," "right," "front," "back," and the like, relate to the subject matter as it is shown in the drawings. However, it is to be understood that the described subject matter may assume various alternative orientations and, accordingly, such terms are not to be considered as limiting.

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

All disclosed ranges are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

All disclosed numerical values are to be understood as being variable from 0-100% in either direction and thus provide support for claims that recite such values or any and all ranges or subranges that can be formed by such values. For example, a stated numerical value of 8 should be understood to vary from 0 to 16 (100% in either direction) and provide support for claims that recite the range itself (e.g., 0 to 16), any subrange within the range (e.g., 2 to 12.5) or any individual value within that range (e.g., 15.2).

What is claimed is:

1. A method of making a bath salt comprising:
   mixing granular magnesium chloride material and a starch material to form an intermediate mixture; and
   mixing a colorant and the intermediate mixture to form the bath salt;
   wherein the colorant uniformly coats the magnesium chloride material; and
   wherein the bath salt is a free flowing solid.

2. The method of claim 1 wherein the bath salt includes 25 wt % to 95 wt % of magnesium chloride material.

3. The method of claim 1 comprising mixing granular magnesium sulfate material, the magnesium chloride material, and the starch material to form the intermediate mixture.

4. The method of claim 3 wherein the bath salt includes 2 wt % to 50 wt % of the magnesium sulfate material.

5. The method of claim 1 comprising mixing granular mineral salt material, the magnesium chloride material, and the starch material to form the intermediate mixture.

6. The method of claim 5 wherein the bath salt includes 1 wt % to 40 wt % of the mineral salt material.

7. The method of claim 5 wherein the mineral salt material includes a natural mineral salt.

8. The method of claim 5 wherein the mineral salt material includes dead sea salt.

9. The method of claim 1 comprising mixing a fragrance enhancing material, the magnesium chloride material, and the starch material to form the intermediate mixture.

10. A method of making a bath salt comprising:
    mixing granular magnesium chloride material and a fragrance enhancing material to form a first intermediate mixture;
    mixing the first intermediate mixture and a starch material to form a second intermediate mixture; and
    mixing the second intermediate mixture and a colorant to form the bath salt;
    wherein the fragrance enhancing material and the colorant uniformly coat the magnesium chloride material; and
    wherein the bath salt is a free flowing solid.

11. The method of claim 10 comprising mixing granular magnesium sulfate material, the magnesium chloride material, and the fragrance enhancing material to form the first intermediate mixture.

12. The method of claim 10 comprising mixing granular mineral salt material, the magnesium chloride material, and the fragrance enhancing material to form the first intermediate mixture.

13. The method of claim 10 comprising mixing granular magnesium sulfate material, granular mineral salt material, the magnesium chloride material, and the fragrance enhancing material to form the first intermediate mixture.

14. The method of claim 13 wherein the bath salt comprises:
    30 wt % to 80 wt % magnesium chloride material;
    5 wt % to 40 wt % magnesium sulfate material; and
    3 wt % to 25 wt % mineral salt material.

15. The method of claim 14 wherein the mineral salt material includes dead sea salt.

16. The method of claim 10 wherein the bath salt includes 25 wt % to 95 wt % of magnesium chloride material.

17. The method of claim 11 wherein the bath salt includes 2 wt % to 50 wt % of the magnesium sulfate material.

18. The method of claim 12 wherein the bath salt includes 1 wt % to 40 wt % of the mineral salt material.

19. The method of claim 12 wherein the mineral salt material includes a natural mineral salt.

20. The method of claim 12 wherein the mineral salt material includes dead sea salt.

* * * * *